United States Patent [19]

Diemer et al.

[11] Patent Number: 4,810,417

[45] Date of Patent: Mar. 7, 1989

[54] PROCESS FOR THE SIMULTANEOUS PRODUCTION OF METHANOL SYNTHESIS GAS AND AMMONIA SYNTHESIS GAS

[75] Inventors: Peter Diemer; Norbert Deuser, both of Essen, Fed. Rep. of Germany

[73] Assignee: Krupp-Koppers GmbH, Essen, Fed. Rep. of Germany

[21] Appl. No.: 456,761

[22] Filed: Jan. 10, 1983

[30] Foreign Application Priority Data

Jan. 21, 1982 [DE] Fed. Rep. of Germany ....... 3201776

[51] Int. Cl.$^4$ .............................................. C10J 3/00
[52] U.S. Cl. .................................. 252/373; 252/376; 252/377; 518/703; 518/705; 423/359
[58] Field of Search ............... 252/373, 374, 376, 377; 518/705, 703; 423/359

[56] References Cited

U.S. PATENT DOCUMENTS

| | | | |
|---|---|---|---|
| 3,418,082 | 12/1968 | Ter Haar | 252/376 |
| 3,872,025 | 3/1975 | Singleton | 252/376 |
| 4,254,094 | 3/1981 | Hegarty | 252/373 |

FOREIGN PATENT DOCUMENTS 1164407  9/1969  United Kingdom ................. 252/373

OTHER PUBLICATIONS

Staege, H. F., "Entrained Bed Gasification", *Hydrocarbon Processing,* Mar. 1982, pp. 92–96.

"Gas Processing Handbook", *Hydrocarbon Processing,* Apr. 1979, p. 153.

*Primary Examiner*—Donald B. Moyer
*Assistant Examiner*—Bruce D. Gray
*Attorney, Agent, or Firm*—Michael J. Striker

[57] ABSTRACT

A process for the simultaneous production of methanol synthesis gas and ammonia synthesis gas proceeds from the crude gas of a coal gasification, which initially is subjected to a $H_2S$-washing at low temperatures. Then follows a splitting of the desulfurized gas into two partial streams, of which one partial stream is led directly into the $CO_2$-washing which serves for production of the methanol-synthesis gas. Another partial stream is in contrast initially subjected to a conversion. From the converted gas then a partial stream is branched off which is provided for the production of ammonia-synthesis gas, whereas the remainder of the converted gas is led into the $CO_2$-washing serving for the production of the methanol-synthesis gas. The partial stream serving for the production of the ammonia-synthesis gas is treated to a separate $CO_2$-washing, in which simultaneously the so-called purge gas from the ammonia-synthesis is led in. The $H_2S$-washing and the $CO_2$-washings are conneced with each other by a common washing agent circulation.

6 Claims, 1 Drawing Sheet

U.S. Patent  Mar. 7, 1989  4,810,417
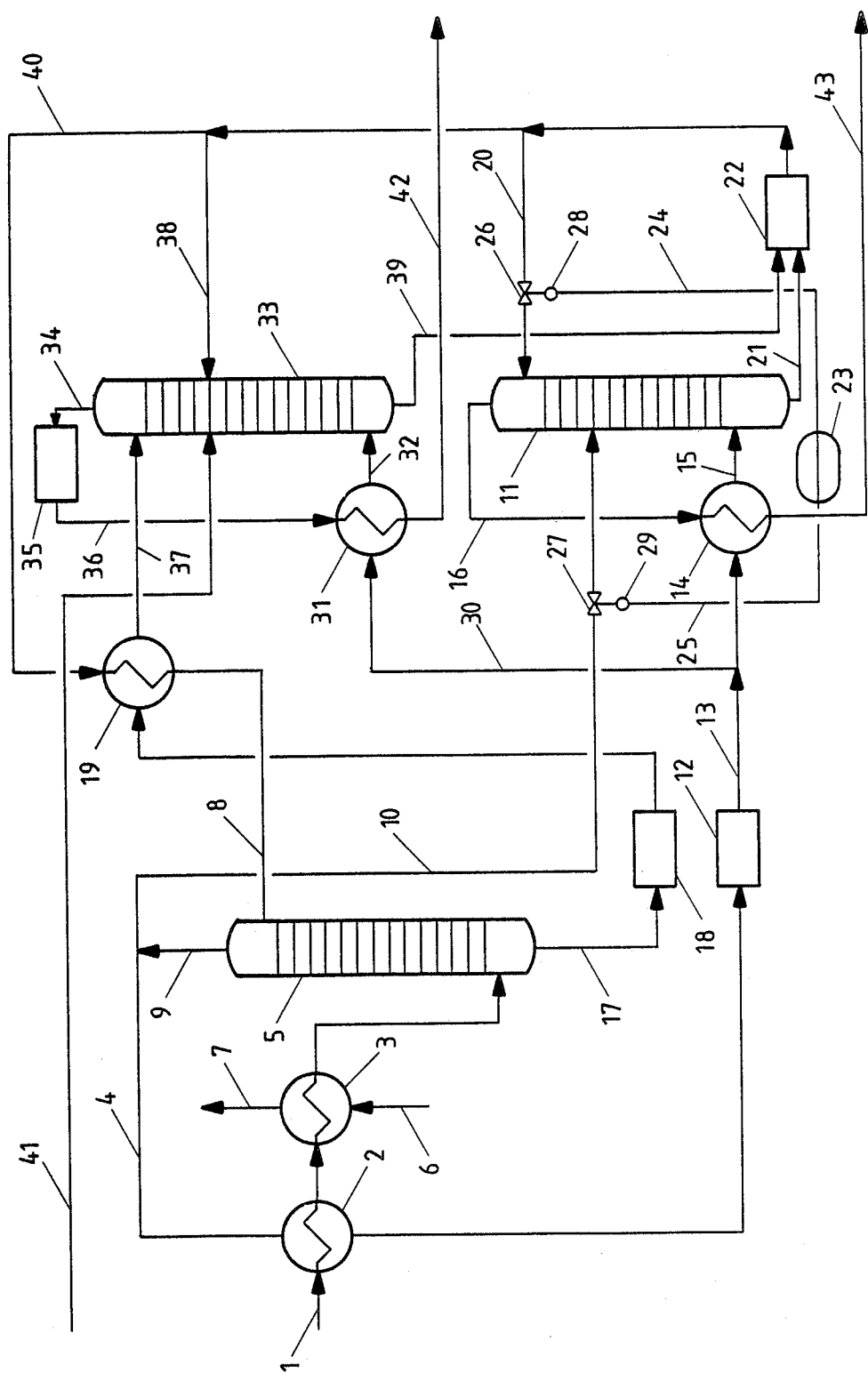

PROCESS FOR THE SIMULTANEOUS PRODUCTION OF METHANOL SYNTHESIS GAS AND AMMONIA SYNTHESIS GAS

BACKGROUND OF THE INVENTION

The invention concerns a process for the simultaneous production of methanol- and ammonia-synthesis gas from the crude gas of a coal gasification by $H_2S$-washing, conversion and $CO_2$ washing of the crude gas, in which the condensed crude gas in connection with the $H_2S$-washing performed at low temperature is split into partial streams, which to different extents are subjected to further gas treatment.

The production of methanol- and/or ammonia-synthesis gas from so-called partial oxidation gas, that is gas, which has been obtained through gasification (partial oxidation) of solid or liquid fuel, has been known for a long time. Indeed according to the type of the therewith employed gasification processes, the gasification of the utilized fuel is performed at different pressures. One known gasification process operating in the low pressure range, that is between about 1 and 1.2 bar, is the Koppers-Totzek process. A particular advantage of this process is that it is useful for the gasification of any coal, independent of its degree of granulation and ash content. In so far as such a coal gasification process is supposed to be employed for the simultaneous production of methanol- and ammonia-synthesis gases, it was previously provided that the produced crude gas (partial oxidation gas), after its cooling in a waste-heat boiler and a direct water washing, initially be condensed in a so-called crude gas compressor up to a pressure of about 30 to 40 bar, and thereupon subsequently subjected to a $H_2S$-washing. For the $H_2S$-washing a so-called low temperature washing is particularly chosen, which operates with a suitable polar organic washing agent, such as for example methanol, in the temperature range between $-20°$ C. and $-60°$ C. In connection with the $H_2S$-washing, the gas is reheated and for purposes of adjusting the optimal composition of the methanol- and ammonia-synthesis gases, split into three partial streams, which to different extents are subjected to further gas treatments. Only the first partial stream is therewith subjected to not only a conversion but also a $CO_2$-washing, whereas the second partial stream is subjected to only a conversion. The third partial stream is, in contrast, subjected to neither a conversion nor a $CO_2$-washing. The so treated partial streams are subsequently reunited and introduced to the methanol synthesis or, after an additional liquid nitrogen washing, led into the ammonia synthesis.

With the methanol synthesis gas, it has however been shown herewith that the residual sulfur content of the partial stream of the gas, which was subjected only to the $H_2S$-washing, as well as the residual sulfur content of the partial stream which was subjected to the $H_2S$-washing and the conversion, are still too high. Since, however, the catalysts employed in the methanol synthesis are extraordinarily sulfur-sensitive, this leads in the long run to a considerable impairment of the methanol synthesis. It was therefore necessary to subject both of the previously mentioned partial streams of the gas before being reunited with the third partial stream to yet an additional treatment, a fine desulfurization, in which its residual sulfur content can be decreased to a value of about 0.1 ppm S. Normally, zinc oxide is employed as fine desulfurization mass. It is obvious that this fine desulfurization, not only in view of the apparatus, but also the operational costs, additionally burdens the processes for the production of methanol synthesis gas.

Previously, in normal fashion that partial stream of the gas was employed for the ammonia synthesis gas, which had run through all of the gas treatment stages. Accordingly, an additional fine desulfurization of the ammonia synthesis gas is as a rule not necessary.

The methanol synthesis gas produced by coal gasification contains inert gas components, essentially nitrogen, argon and methane, which must be excluded from the methanol synthesis. The gas excluded from the methanol synthesis is therewith normally designated as purge gas. It contains, in addition to the already mentioned inert gas component, also carbon dioxide as well as the valuable products hydrogen, methanol and carbon monoxide. Previously, this purge gas was either used as heating gas, or in additional apparatus the hydrogen was recovered from the purge gas. It is obvious that the purge gas is too valuable for combustion, and that the additional apparatus for the recovery of hydrogen from the purge gas additionally burdens not only the apparatus but also the operational costs of the entire process for the simultaneous production of methanol- and ammonia-synthesis gases.

SUMMARY OF THE INVENTION

The invention is therefore based upon the object of improving the processes for the simultaneous production of methanol- and ammonia-synthesis gases from the crude gas of a coal gasification, to the effect that a fine desulfurization of the methanol-synthesis gas can be avoided and simultaneously the combustion of the so-called purge gas is avoided, and this instead is led to a utilization which avoids additional apparatus and operational costs.

This object is attained according to the present invention by a process of the above described type, characterized in that (a) the cold gas stream leaving the $H_2S$-washing is initially split into two partial streams, of which one partial stream is led directly into the upper or middle part of a $CO_2$-washing driven at low temperatures, which serves for the treatment of the gas stream provided for the production of methanol-synthesis gas (so-called $CO_2$-washing 1), whereas the other partial stream, after appropriate reheating, is converted, whereupon from the converted gas a partial stream is branched off, which is provided for the production of ammonia-synthesis gas, while the remaining residue of the converted gas, after an appropriate recooling, is led into the lower part of the $CO_2$-washing 1;

(b) the gas stream leaving the $CO_2$-washing 1 is introduced to the methanol synthesis without further after-desulfurization;

(c) the partial stream of the converted gas provided for the production of ammonia-synthesis gas is led into the lower part of a $CO_2$-washing, likewise operated at low temperatures (so-called $CO_2$-washing 2), whereby simultaneously the purge gas coming from the methanol synthesis is led into the upper or middle part of this $CO_2$-washing;

(d) the $H_2S$-washing, as well as the $CO_2$-washings 1 and 2, are connected with each other by a common washing agent circulation, in such fashion that the regenerated washing agent coming from the $H_2S$-washing is delivered to the upper part of $CO_2$-washing 2, while a part of the stripped washing agent coming from the $CO_2$-washings 1 and 2 is delivered to the $H_2S$-washing, whereas the other part of the stripped washing agent is redelivered to the $CO_2$-washings 1 and 2; and (e) the gas stream leaving the $CO_2$-washing 2 is subjected to a liquid nitrogen washing and then introduced to the ammonia synthesis.

That is, with the process according to the present invention two separated from one another $CO_2$-washings (1 and 2) are provided for the methanol- and the ammonia-synthesis gas, which are supplied with different gas streams, the cold gas stream leaving the common $H_2S$-washing being therewith initially split into two partial streams, of which the one partial stream is led directly into the upper or middle part of the $CO_2$-washing 1, which is responsibe for the treatment of the gas stream provided for the production of methanol-synthesis gas. The other partial stream of the desulfurized gas is converted, and in connection therewith subjected to a further partitioning. Herewith normally between 99 and 70 volume-% of the cold gas leaving the $H_2S$-washing is introduced to the conversion. Then subsequently a part of the converted gas is branched off for the production of ammonia-synthesis gas, whereas the remaining residue is led into the bottom part of the $CO_2$-washing 1. The amount of the partial stream of the converted gas branched off for the production of ammonia-synthesis gas depends in practice naturally upon the requirements and behavior of the synthesis plants. Theoretically, however, between 99 and 1 volume-% of the converted gas can be branched off for the production of ammonia-synthesis gas. The methanol-synthesis gas can therewith be discharged from the top of the $CO_2$-washing 1, and requires no additional fine desulfurization, since through the manner of operation according to the present invention a nearly complete desulfurization of the methanol-synthesis gas is obtained.

The partial stream of the converted gas provided for the production of ammonia-synthesis gas is led into the lower part of the $CO_2$-washing 2 provided therefor, into which simultaneously is led at the upper or middle part, the purge gas coming from the methanol synthesis. Through this manner of operation almost the entire hydrogen contained in the purge gas can be utilized for the ammonia synthesis, and the methanol contained therein is simultaneously introduced to the methanol circulation of the gas washings. That is the purge gas is here actually in logical manner introduced to a utilization, without having therewith arise additional plant and operational costs. The gas stream leaving across the top from the $CO_2$-washing 2 can, after it has been subjected to a liquid nitrogen washing, be introduced to its further working-up as ammonia-synthesis gas.

The novel features which are considered characteristic for the invention are set forth in particular in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

The single FIGURE is a schematically represented flow chart for the process according to the present invention. The flow chart shows only the apparatus parts unconditionally necessary for illustration of the process, whereas additional arrangements as well as the apparatus for coal gasification, methanol synthesis and ammonia synthesis are not represented.

DESCRIPTION OF THE PREFERRED EMBODIMENTS

The following operational Example concerns the working up of an amount of crude gas of about 158,000 Nm$^3$/h, which arises upon the gasification of 88.6 t/h ash- and water-free coal according to the Koppers-Totzek process at a pressure of 1.1 bar. The crude gas, which after cooling down and direct water washing has been condensed in the crude gas condenser (not represented in the drawing) up to a pressure of 38 bar, has the following composition:

| | |
|---|---|
| $CO_2$ | 10.6 vol. % |
| CO | 62.5 vol. % |
| $H_2$ | 24.6 vol. % |
| $H_2S$ | 0.4 vol. % |
| COS | 0.1 vol. % |
| $N_2$, Ar + $CH_4$ | 1.8 vol. % |

The crude gas coming from the crude gas condenser is led across conduit 1 into the heat exchanger 2 as well as thereupon subsequently into the gas low temperature cooler 3. Herewith the crude gas is initially pre-cooled in indirect heat exchange in heat exchanger 2 with the gas coming from column 5, flowing in conduit 4, whereupon subsequently the low temperature cooling of the crude gas follows in gas low temperature cooler 3 to a temperature of −30° C. to −40° C., which for this purpose is supplied with a cooling agent across conduit 6, which is again discharged across conduit 7. With the mentioned low temperature the crude gas is then led into the lower part of column 5 provided with components (plates), which serves as the $H_2S$-washing. Herewith in addition to the $H_2S$, naturally also other sulfur compounds such as COS and $CS_2$ are removed from the crude gas. The $H_2S$-washing is performed with methanol, which at a temperature of −40° C. is introduced across conduit 8, and is delivered at the top to column 5. In column 5 the crude gas is desulfurized to a sulfur content of about 1 ppm, and it is discharged at a temperature of −38° C. through conduit 9 across the top from column 5.

The cold gas stream in conduit 9 is then split into two partial streams, of which the one partial stream is led directly across conduit 10 into the upper or middle part of the column 11, likewise provided with components (plates), which serves as the $CO_2$-washing 1. Herewith the volume of the gas stream in conduit 10 amounts to about 16 volume-% of the total amount of gas provided in conduit 9. The introduction of this partial stream into column 11 follows herewith at a height of the thirteenth plate from the top.

The second partial stream, which contains the residual amount of gas from conduit 9, is meanwhile discharged across conduit 4 and led across heat exchanger 2 to the conversion apparatus 12. In heat exchanger 2 the gas is subjected to a reheating up to 25° C. In the conversion plant 12 the CO present in the gas is reacted according to the so-called conversion reaction

Further details of the conversion plant 12 are not necessary here. It involves, however, a typical commercial plant which works according to principles known in the art. The conversion follows in the present case in the presence of water vapor at a temperature from 300° to 500° C. on an iron-chromium catalyst. The converted and de-moisturized gas leaves the conversion plant 12 across conduit 13 and has the following composition

| | |
|---|---|
| $CO_2$ | 43.1 vol. % |
| CO | 3.0 vol. % |
| $H_2$ | 52.7 vol. % |
| $N_2$, Ar + $CH_4$ | 1.2 vol. % |

From conduit 13 branches off conduit 30, through which about 64 volume-% of the converted gas, which is provided for the production of ammonia-synthesis gas, are branched off. The residual part of the converted gas is cooled in heat exchanger 14 in indirect heat exchange with the methanol-synthesis gas in conduit 16, to a temperature of about −30° C. With this temperature the gas is led across conduit 15 into the bottom part of column 11. The $CO_2$-washing 1 in column 11 is likewise performed with methanol at low temperatures. In addition to the $CO_2$-removal, herewith simultaneously a practically complete desulfurization of the gas is obtained, so that the gas stream leaving across conduit 16 at the head of column 11 displays only still a residual sulfur content which lies below 0.1 ppm S. This gas can therefore without further fine desulfurization be employed as methanol-synthesis gas, and is led accordingly, after passing the heat exchanger 14, to the not represented methanol synthesis plant. Herewith, across conduit 43, per hour about 66,800 $Nm^3$ methanol-synthesis gas is discharged with the following composition:

| | |
|---|---|
| $CO_2$ | 3.1 vol. % |
| CO | 26.7 vol. % |
| $H_2$ | 68.2 vol. % |
| $N_2$, Ar + $CH_4$ | 2.0 vol. % |

The partial stream discharged across conduit 30 of about 64 vol.-% of the converted gas is meanwhile cooled down in heat exchanger 31 in indirect heat exchange with the ammonia-synthesis gas in conduit 36 to a temperature of about −40° C. At this temperature it is led across conduit 32 into the lower part of column 33 provided with components (plates), in which the so-called $CO_2$-washing 2 is performed. Across conduit 41, after appropriate cooling down, simultaneously about 22,000 $Nm^3$ of the purge gas coming from the not represented methanol synthesis is led into the middle part of column 33 at the height of the fiftieth plate from the top. The purge gas in conduit 41 has a pressure of about 32 bar and the following composition:

| | |
|---|---|
| $CO_2$ | 4.0 vol. % |
| CO | 19.5 vol. % |
| $H_2$ | 69.2 vol. % |
| $N_2$, Ar, $CH_4$ | 6.3 vol. % |
| methanol | 1.0 vol. % |

The $CO_2$-washing 2 in column 33 is likewise performed with methanol at low temperatures. In addition to the $CO_2$-removal, herewith simultaneously a practically complete desulfurization of the converted gas is obtained. The purge gas is already sulfur-free. From this in $CO_2$-washing 2 the $CO_2$ and the methanol are removed. The provision of the methanol necessary for $CO_2$-removal and desulfurization follows in column 33 at two different places, namely across conduit 37 and conduit 38.

Herewith is delivered across conduit 37 to the top of column 33 so-called regenerated methanol. This methanol arises from column 5, from the sump of which it is discharged across conduit 17 and led into the regenerating arrangement 18. There follows the distillative regeneration of the methanol in known manner by heat treatment at a temperature of about 95° C. The regenerated methanol, which is discharged from the regeneration arrangement 18 across conduit 37, must before entry into column 33 naturally be subjected to an appropriate re-cooling in heat exchanger 19, so that it can enter into column 33 through conduit 37 with a temperature of about −54° C.

Across conduit 38 moreover a partial stream of the stripped methanol flowing in conduit 40 is delivered to column 33. The entry place of conduit 38 into column 33 lies about 40 plates below the entry place of conduit 37. The methanol in conduit 40 arises from columns 11 and 33, from the sumps of which it is discharged across conduits 21 and 39 and led into the stripper 22. There the methanol is freed of the withdrawn gaseous components by stripping, i.e. through the blowing in of inert gas under decreased pressure. The stripped methanol is discharged from the stripper 22 across conduit 40, which leads across heat exchanger 19 and conduit 8 to column 5, and closes the methanol circulation among the three columns 5, 11 and 33. The stripping of the methanol follows at a temperature of about −60° C., so that an additional cooling thereof upon its re-introduction into columns 11 and 33 is not necessary.

The methanol necessary for the $CO_2$-removal and desulfurization in the $CO_2$-washing 1 is delivered across conduit 20 to the top of column 11. Herewith is involved a stripped methanol from conduit 40, which flows through column 11 from top to bottom and at the sump thereof is again discharged through conduit 21. Across this conduit the methanol is led back into the already mentioned stripper 22.

The gas stream leaving across the top from column 33 is discharged across conduit 34 and led initially into the liquid nitrogen washing 35 and then subsequently across conduit 36 into the heat exchanger 31. After passing therethrough the gas can be introduced across conduit 42 into the not represented ammonia synthesis plant. Herewith across conduit 42 per hour about 110,900 $Nm^3$ ammonia synthesis gas is discharged with the following composition:

| | |
|---|---|
| $H_2$ | 75 vol. % |
| $N_2$ | 25 vol. % |

The composition of the produced methanol-synthesis gas is automatically supervised by a measuring station 23 installed into conduit 43. The measuring station 23 is herewith connected across impulse conduits 24 and 25 with the regulating valves 26 and 27, which are installed in conduits 10 and 20. Herewith the $CO_2$-content in the methanol-synthesis gas is regulated by the amount of stripped methanol which is delivered across conduit 20 to the column 11. When the determined $CO_2$-content according to measuring station 23 exceeds the previously set nominal value, an impulse is sent which is carried across impulse conduit 24 to the step motor 28 belonging to regulating valve 26, and which leads to a further opening of regulating valve 26. Thereby naturally the amount of stripped methanol delivered across conduit 20 to column 11 is increased, which naturally leads to an improved $CO_2$-washing out in column 11. With a drop of the $CO_2$-content below the previously set nominal value, the regulation naturally follows in the reverse sense. That is, through a corresponding operation of the regulating valve 26, the influx of stripped methanol across conduit 20 into column 11 is throttled. In normal manner it can be provided that the methanol partial stream discharged across conduit 20 lies in the order of magnitude of about 1.9 K Mol $CH_3OH$ per K Mol gas.

The regulation of the desired ratio of gas components in the methanol-synthesis gas $$\frac{H_2 - CO_2}{CO + CO_2} \geqq 2$$

follows by influencing the amount of gas which is led across conduit 10 directly from column 5 ($H_2S$-washing) into column 11 ($CO_2$-washing 1). When the data determined at measuring station 23 which can be evaluated by a process computer provides for the above given ratio of gas components a value of less than two, then the supply of unconverted gas across conduit 10 into column 11 must be throttled. Therewith again a corresponding impulse is sent which is carried across impulse conduit 25 to the step motor 29 belonging to regulating valve 27, and which leads to a corresponding throttling of the regulating valve 27. Thereby naturally the supply of unconverted gas into column 11 is decreased, whereas simultaneously the partial stream of gas which is introduced across conduit 4 to the conversion apparatus 12 is subjected to a corresponding increase. To the extent that the mentioned ratio of gas components should however exceed substantially the value two, then the regulation can naturally also follow in the reverse sense, whereby the supply of unconverted gas into column 11 is increased and the partial stream of converted gas is decreased. In normal manner, one can proceed to maintain the ratio $$\frac{H_2 - CO_2}{CO + CO_2} \geqq 2$$

when the partial stream of unconverted gas, which is introduced across conduit 10 directly into the $CO_2$-washing 1 in column 11 amounts to between 30 and 40 vol.-% of the converted gas, which is introduced into column 11 across conduit 15.

In this process example, the $H_2S$- and $CO_2$-washings employ methanol as washing agent. Obviously these washings can also be performed with another suitable washing agent, particularly with polar organic liquids. Generally methanol represents the preferred washing agent, since through the introduction of purge gas into column 33 the methanol contained therein can be recovered and can be introduced into the washing agent circulation. Thereby any losses of washing agent can be practically balanced out.

The usefulness of the process according to the present invention is naturally also the same when, instead of coal, another fuel such as e.g. pitch, tar, peat or heavy oil is used as entry material for the gasification.

It will be understood that each of the elements described above, or two or more together, may also find a useful application in other types of gas productions differing from the types described above.

While the invention has been described and illustrated as embodied in a process for the simultaneous production of methanol synthesis gas and ammonia synthesis gas, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. In a process for the simultaneous production of methanol synthesis gas and of ammonia synthesis gas from the crude gas of a coal gasification by means of $H_2S$-washing, conversion and $CO_2$-washing of the crude gas, in which the condensed crude gas in split into partial streams after the $H_2S$-washing performed at low temperatures, which partial streams are subjected to the further gas treatment to differing extents, the improvement comprising (a) splitting the cold gas stream leaving the $H_2S$-washing initially into two partial streams, of which one partial stream is led directly into the upper or middle part of a first $CO_2$-washing operated at low temperatures, which serves for treatment of the gas stream provided for production of methanol-synthesis gas, while the other partial stream after appropriate reheating is converted, whereupon from the converted gas a partial stream is branched off which is provided for the production of ammonia-synthesis gas, while the rest of the converted gas after appropriate re-cooling is led into the lower part of said first $CO_2$-washing;

(b) introducing the gas stream leaving said first $CO_2$-washing without further after-desulfurization to a methanol synthesis;

(c) leading the partial stream of converted gas provided for the production of ammonia-synthesis gas into the lower part of a second $CO_2$-washing, likewise operated at low temperatures, while simultaneously introducing purge gas coming from the methanol synthesis into the upper or middle part of this second $CO_2$-washing;

(d) connecting the $H_2S$-washing and the first and second $CO_2$-washings with each other by a common washing agent circulation so that regenerated washing agent coming from the $H_2S$-washing is delivered to the top part of the second $CO_2$-washing, while a part of the stripped washing agent coming from the first and second $CO_2$-washing is delivered to the $H_2S$-washing, and while the other part of the stripped washing agent is redelivered to the first and second $CO_2$-washings; and (e) subjecting the gas stream leaving the second $CO_2$-washing to a liquid nitrogen washing and then introducing said gas stream to an ammonia synthesis.

2. Process according to claim 1, wherein for the $H_2S$-washing as well as the first and second $CO_2$-washings, methanol is used at temperatures between $-20°$ C. and $-60°$ C.

3. Process according to claim 1, wherein of the cold gas stream leaving the $H_2S$-washing, between 99 and 70 volume percent is led to the conversion, while the remainder is led directly into the first $CO_2$-washing.

4. Process according to claim 1, further comprising regulating the $CO_2$-content in the produced methanol-synthesis gas by adjusting the amount of stripped washing agent which is re-delivered to the first $CO_2$-washing.

5. Process according to claim 1, further comprising adjusting in the produced methanol-synthesis gas the desired ratio of gas components $$\frac{H_2 - CO_2}{CO + CO_2} \geq 2$$

by regulation of the amount of gas which is led from the $H_2S$-washing directly into the upper or middle part of the first $CO_2$-washing.

6. Process according to claim 1, wherein the reheating of the gas before the conversion follows in heat exchange with the condensed crude gas, and the re-cooling of the converted gas follows in heat exchange with the methanol-synthesis gas leaving the first $CO_2$-washing or the ammonia-synthesis gas leaving the liquid nitrogen washing.

* * * * *